US009106958B2

United States Patent
el Kaliouby et al.

(10) Patent No.: US 9,106,958 B2
(45) Date of Patent: Aug. 11, 2015

(54) VIDEO RECOMMENDATION BASED ON AFFECT

(75) Inventors: Rana el Kaliouby, Waltham, MA (US); Richard Scott Sadowsky, Sturbridge, MA (US); Rosalind Wright Picard, Newtonville, MA (US); Oliver Orion Wilder-Smith, Holliston, MA (US); May Bahgat, New Cairo (EG)

(73) Assignee: Affectiva, Inc., Waltham, MA (US)

( * ) Notice: Subject to any disclaimer, the term of this patent is extended or adjusted under 35 U.S.C. 154(b) by 0 days.

(21) Appl. No.: 13/406,068

(22) Filed: Feb. 27, 2012

(65) Prior Publication Data
US 2012/0222058 A1   Aug. 30, 2012

Related U.S. Application Data

(60) Provisional application No. 61/447,089, filed on Feb. 27, 2011, provisional application No. 61/447,464, filed on Feb. 28, 2011, provisional application No. 61/467,209, filed on Mar. 24, 2011, provisional application No. 61/549,560, filed on Oct. 20, 2011, provisional application No. 61/568,130, filed on Dec. 7, 2011, provisional application No. 61/580,880, filed on Dec. 28, 2011, provisional application No. 61/581,913, filed on Dec. 30, 2011.

(51) Int. Cl.
| | |
|---|---|
| H04H 60/33 | (2008.01) |
| H04N 21/466 | (2011.01) |
| H04N 21/25 | (2011.01) |
| H04N 21/4223 | (2011.01) |
| A61B 5/16 | (2006.01) |
| G06Q 30/06 | (2012.01) |

(52) U.S. Cl.
CPC ............ *H04N 21/4668* (2013.01); *A61B 5/165* (2013.01); *G06Q 30/0631* (2013.01); *H04N 21/251* (2013.01); *H04N 21/4223* (2013.01)

(58) Field of Classification Search
None
See application file for complete search history.

(56) References Cited

U.S. PATENT DOCUMENTS

| 3,034,500 A | 5/1962 | Backster, Jr. |
| 3,548,806 A | 12/1970 | Fisher |

(Continued)

FOREIGN PATENT DOCUMENTS

| JP | 08115367 | 7/1996 |
| KR | 10-2005-0021759 A | 3/2005 |

(Continued)

OTHER PUBLICATIONS

Fragopanagos et al., Emotion recognition in human-computer interaction, Emotion and Brain, Neural Networks 2005, Elsevier Ltd, pp. 389-405.*

(Continued)

*Primary Examiner* — John Schnurr
*Assistant Examiner* — Cynthia Fogg
(74) *Attorney, Agent, or Firm* — Adams Intellex, PLC

(57) ABSTRACT

Analysis of mental states is provided to enable data analysis pertaining to video recommendation based on affect. Video response may be evaluated based on viewing and sampling various videos. Data is captured for viewers of a video where the data includes facial information and/or physiological data. Facial and physiological information may be gathered for a group of viewers. In some embodiments, demographics information is collected and used as a criterion for visualization of affect responses to videos. In some embodiments, data captured from an individual viewer or group of viewers is used to rank videos.

26 Claims, 9 Drawing Sheets

(56) References Cited

U.S. PATENT DOCUMENTS

| | | | |
|---|---|---|---|
| 3,870,034 A | 3/1975 | James | |
| 4,353,375 A | 10/1982 | Colburn et al. | |
| 4,448,203 A | 5/1984 | Williamson et al. | |
| 4,794,533 A | 12/1988 | Cohen | |
| 4,807,642 A | 2/1989 | Brown | |
| 4,817,628 A | 4/1989 | Zealear et al. | |
| 4,950,069 A | 8/1990 | Hutchinson | |
| 4,964,411 A | 10/1990 | Johnson et al. | |
| 5,016,282 A | 5/1991 | Tomono et al. | |
| 5,031,228 A | 7/1991 | Lu | |
| 5,219,322 A | 6/1993 | Weathers | |
| 5,247,938 A | 9/1993 | Silverstein et al. | |
| 5,259,390 A | 11/1993 | Maclean | |
| 5,507,291 A | 4/1996 | Stirbl et al. | |
| 5,572,596 A | 11/1996 | Wildes et al. | |
| 5,619,571 A | 4/1997 | Sandstrom et al. | |
| 5,647,834 A | 7/1997 | Ron | |
| 5,649,061 A | 7/1997 | Smyth | |
| 5,663,900 A | 9/1997 | Bhandari et al. | |
| 5,666,215 A | 9/1997 | Fredlund et al. | |
| 5,725,472 A | 3/1998 | Weathers | |
| 5,741,217 A | 4/1998 | Gero | |
| 5,760,917 A | 6/1998 | Sheridan | |
| 5,762,611 A | 6/1998 | Lewis et al. | |
| 5,772,591 A | 6/1998 | Cram | |
| 5,774,591 A | 6/1998 | Black et al. | |
| 5,802,220 A | 9/1998 | Black et al. | |
| 5,825,355 A | 10/1998 | Palmer et al. | |
| 5,886,683 A | 3/1999 | Tognazzini et al. | |
| 5,898,423 A | 4/1999 | Tognazzini et al. | |
| 5,920,477 A | 7/1999 | Hoffberg et al. | |
| 5,945,988 A | 8/1999 | Williams et al. | |
| 5,959,621 A | 9/1999 | Nawaz et al. | |
| 5,969,755 A | 10/1999 | Courtney | |
| 5,983,129 A | 11/1999 | Cowan et al. | |
| 5,987,415 A | 11/1999 | Breese et al. | |
| 6,004,061 A | 12/1999 | Manico et al. | |
| 6,004,312 A | 12/1999 | Finneran et al. | |
| 6,008,817 A | 12/1999 | Gilmore, Jr. | |
| 6,026,321 A | 2/2000 | Miyata et al. | |
| 6,026,322 A | 2/2000 | Korenman et al. | |
| 6,056,781 A | 5/2000 | Wassick et al. | |
| 6,067,565 A | 5/2000 | Horvitz | |
| 6,088,040 A | 7/2000 | Oda et al. | |
| 6,099,319 A | 8/2000 | Zaltman et al. | |
| 6,134,644 A | 10/2000 | Mayuzumi et al. | |
| 6,182,098 B1 | 1/2001 | Selker | |
| 6,185,534 B1 | 2/2001 | Breese et al. | |
| 6,195,651 B1 | 2/2001 | Handel et al. | |
| 6,212,502 B1 | 4/2001 | Ball et al. | |
| 6,222,607 B1 | 4/2001 | Szajewski et al. | |
| 6,309,342 B1 | 10/2001 | Blazey et al. | |
| 6,327,580 B1 | 12/2001 | Pierce et al. | |
| 6,349,290 B1 | 2/2002 | Horowitz et al. | |
| 6,351,273 B1 | 2/2002 | Lemelson et al. | |
| 6,437,758 B1 | 8/2002 | Nielsen et al. | |
| 6,443,840 B2 | 9/2002 | Von Kohorn | |
| 6,530,082 B1 | 3/2003 | Del Sesto et al. | |
| 6,577,329 B1 | 6/2003 | Flickner et al. | |
| 6,629,104 B1 | 9/2003 | Parulski et al. | |
| 6,655,963 B1 * | 12/2003 | Horvitz et al. | 434/236 |
| 6,792,458 B1 | 9/2004 | Muret et al. | |
| 6,847,376 B2 | 1/2005 | Engeldrum et al. | |
| 7,013,478 B1 * | 3/2006 | Hendricks et al. | 725/46 |
| 7,113,916 B1 | 9/2006 | Hill | |
| 7,120,880 B1 | 10/2006 | Dryer et al. | |
| 7,197,459 B1 | 3/2007 | Harinarayan et al. | |
| 7,233,684 B2 | 6/2007 | Fedorovskaya et al. | |
| 7,246,081 B2 | 7/2007 | Hill | |
| 7,263,474 B2 | 8/2007 | Fables et al. | |
| 7,266,582 B2 | 9/2007 | Stelting | |
| 7,307,636 B2 | 12/2007 | Matraszek et al. | |
| 7,327,505 B2 | 2/2008 | Fedorovskaya et al. | |
| 7,350,138 B1 | 3/2008 | Swaminathan et al. | |
| 7,353,399 B2 | 4/2008 | Ooi et al. | |
| 7,355,627 B2 | 4/2008 | Yamazaki et al. | |
| 7,428,318 B1 | 9/2008 | Madsen et al. | |
| 7,496,622 B2 | 2/2009 | Brown et al. | |
| 7,549,161 B2 | 6/2009 | Poo et al. | |
| 7,551,755 B1 | 6/2009 | Steinberg et al. | |
| 7,555,148 B1 | 6/2009 | Steinberg et al. | |
| 7,558,408 B1 | 7/2009 | Steinberg et al. | |
| 7,564,994 B1 | 7/2009 | Steinberg et al. | |
| 7,573,439 B2 | 8/2009 | Lau et al. | |
| 7,580,512 B2 | 8/2009 | Batni et al. | |
| 7,584,435 B2 | 9/2009 | Bailey et al. | |
| 7,587,068 B1 | 9/2009 | Steinberg et al. | |
| 7,610,289 B2 | 10/2009 | Muret et al. | |
| 7,620,934 B2 | 11/2009 | Falter et al. | |
| 7,644,375 B1 | 1/2010 | Anderson et al. | |
| 7,676,574 B2 | 3/2010 | Glommen et al. | |
| 7,747,801 B2 | 6/2010 | Han et al. | |
| 7,826,657 B2 | 11/2010 | Zhang et al. | |
| 7,830,570 B2 | 11/2010 | Morita et al. | |
| 7,949,561 B2 | 5/2011 | Briggs | |
| 8,010,458 B2 | 8/2011 | Galbreath et al. | |
| 8,046,798 B1 * | 10/2011 | Schlack et al. | 725/46 |
| 8,401,248 B1 | 3/2013 | Moon et al. | |
| 2001/0033286 A1 | 10/2001 | Stokes et al. | |
| 2001/0041021 A1 | 11/2001 | Boyle et al. | |
| 2002/0007249 A1 | 1/2002 | Cranley | |
| 2002/0030665 A1 | 3/2002 | Ano | |
| 2002/0042557 A1 | 4/2002 | Bensen et al. | |
| 2002/0054174 A1 | 5/2002 | Abbott et al. | |
| 2002/0084902 A1 | 7/2002 | Zadrozny et al. | |
| 2002/0171551 A1 | 11/2002 | Eshelman et al. | |
| 2002/0178440 A1 * | 11/2002 | Agnihotri et al. | 725/10 |
| 2002/0182574 A1 | 12/2002 | Freer | |
| 2003/0035567 A1 | 2/2003 | Chang et al. | |
| 2003/0037041 A1 | 2/2003 | Hertz | |
| 2003/0093784 A1 * | 5/2003 | Dimitrova et al. | 725/10 |
| 2003/0191682 A1 | 10/2003 | Shepard et al. | |
| 2004/0181457 A1 | 9/2004 | Biebesheimer et al. | |
| 2005/0071865 A1 * | 3/2005 | Martins | 725/10 |
| 2005/0187437 A1 | 8/2005 | Matsugu et al. | |
| 2005/0289582 A1 * | 12/2005 | Tavares et al. | 725/10 |
| 2006/0019224 A1 | 1/2006 | Behar et al. | |
| 2006/0143647 A1 * | 6/2006 | Bill | 725/10 |
| 2006/0235753 A1 | 10/2006 | Kameyama | |
| 2007/0162505 A1 * | 7/2007 | Cecchi et al. | 707/104.1 |
| 2007/0255831 A1 | 11/2007 | Hayashi et al. | |
| 2007/0299964 A1 | 12/2007 | Wong et al. | |
| 2008/0091512 A1 | 4/2008 | Marci et al. | |
| 2008/0091515 A1 | 4/2008 | Thieberger et al. | |
| 2008/0101660 A1 | 5/2008 | Seo | |
| 2008/0103784 A1 | 5/2008 | Wong et al. | |
| 2008/0208015 A1 | 8/2008 | Morris et al. | |
| 2008/0214903 A1 | 9/2008 | Orbach | |
| 2008/0222671 A1 * | 9/2008 | Lee et al. | 725/10 |
| 2008/0295126 A1 | 11/2008 | Lee et al. | |
| 2009/0006206 A1 | 1/2009 | Groe et al. | |
| 2009/0083421 A1 | 3/2009 | Glommen et al. | |
| 2009/0094286 A1 | 4/2009 | Lee et al. | |
| 2009/0133048 A1 * | 5/2009 | Gibbs et al. | 725/14 |
| 2009/0150919 A1 * | 6/2009 | Lee et al. | 725/10 |
| 2009/0177528 A1 | 7/2009 | Wu et al. | |
| 2009/0271417 A1 | 10/2009 | Toebes et al. | |
| 2009/0299840 A1 | 12/2009 | Smith | |
| 2010/0030645 A1 * | 2/2010 | Watanuki et al. | 705/14.53 |
| 2010/0070523 A1 | 3/2010 | Delgo et al. | |
| 2010/0099955 A1 | 4/2010 | Thomas et al. | |
| 2010/0266213 A1 | 10/2010 | Hill | |
| 2010/0274847 A1 | 10/2010 | Anderson et al. | |
| 2010/0281497 A1 | 11/2010 | Miyazaki | |
| 2011/0092780 A1 | 4/2011 | Zhang et al. | |
| 2011/0143728 A1 | 6/2011 | Holopainen et al. | |
| 2011/0196855 A1 | 8/2011 | Wable et al. | |
| 2011/0231240 A1 | 9/2011 | Schoen et al. | |
| 2011/0263946 A1 | 10/2011 | El Kaliouby et al. | |
| 2011/0301433 A1 | 12/2011 | Sadowsky et al. | |
| 2012/0030696 A1 * | 2/2012 | Smith | 725/10 |
| 2012/0072939 A1 * | 3/2012 | Crenshaw | 725/12 |

(56) References Cited

U.S. PATENT DOCUMENTS

2012/0093481 A1* 4/2012 McDowell et al. .......... 386/241
2013/0006625 A1* 1/2013 Gunatilake et al. .......... 704/235

FOREIGN PATENT DOCUMENTS

| KR | 10-2008-0016303 A | 2/2008 |
| KR | 10-2010-0021702 A | 2/2010 |
| KR | 1020100048688 A | 5/2010 |
| KR | 100964325 B1 | 6/2010 |
| KR | 1020100094897 A | 8/2010 |
| KR | 10-2011-0047718 A | 5/2011 |
| NL | WO 02/43391 A1 | 5/2002 |
| WO | WO 2011/045422 A1 | 4/2011 |

OTHER PUBLICATIONS

Spiros et al., Emotion recognition through facial expression analysis based on a neruofuzzy network, Emotion and Brain, Neural Network 2005, Elsevier Ltd, pp. 423-435.*

Maaoui et al., Emotion Recognition for Human-Machine Communication, 2008 IEEE/RS J International Conference on Intelligent Robots and Systems, Sep. 22-26, 2008, pp. 1211-1214.*

Rana Ayman El Kaliouby, Mind-reading machines: automated inference of complex mental states, Jul. 2005, University of Cambridge, Cambridge, United Kingdom.

International Search Report dated Nov. 14, 2011 for PCT/US2011/039282.

International Search Report dated Apr. 16, 2012 for PCT/US2011/054125.

International Search Report dated May 24, 2012 for PCT/US2011/060900.

International Search Report dated Nov. 29, 2012 for PCT/US2012/026805.

International Search Report dated May 15, 2013 for PCT/US2012/068496.

The State Intellectual Property Office of China Office Action dated Jul. 23, 2014 for Application No. 201180053869.7.

* cited by examiner

VIDEO RECOMMENDATION BASED ON AFFECT

RELATED APPLICATIONS

This application claims the benefit of U.S. provisional patent applications "Recommendation and Visualization of Affect Responses to Videos" Ser. No. 61/447,089, filed Feb. 27, 2011, "Video Ranking Based on Affect" Ser. No. 61/447,464, filed Feb. 28, 2011, "Baseline Face Analysis" Ser. No. 61/467,209, filed Mar. 24, 2011, "Mental State Analysis of Voters" Ser. No. 61/549,560, filed Oct. 20, 2011, "Mental State Evaluation Learning for Advertising" Ser. No. 61/568,130, filed Dec. 7, 2011, "Affect Based Concept Testing" Ser. No. 61/580,880, filed Dec. 28, 2011, and "Affect Based Evaluation of Advertisement Effectiveness" Ser. No. 61/581,913, filed Dec. 30, 2011. This application is also related to "Visualization of Affect Responses to Videos" Ser. No. 13/405,842, filed on the same day as the present application on Feb. 27, 2012. Each of the foregoing applications is hereby incorporated by reference in its entirety.

FIELD OF INVENTION

This application relates generally to analysis of mental states and more particularly to making video recommendations based on affect.

BACKGROUND

People spend a tremendous amount of time engaged in viewing and interacting with videos. The videos may be watched in numerous contexts including education, entertainment, obtaining daily news, watching the latest movies, and many others. A video may be a movie, a television show, a web series, a webisode, a video, a music video, or a video clip. The video may be viewed as a stand-alone element on an electronic display, or may be part of a webpage. Evaluation of these videos and people's responses to them is exceedingly important to gauging the effectiveness of education, commerce, and entertainment. People can self-rate videos in a tedious fashion of entering a specific number of stars corresponding to a level of like or dislike, or may even answer a list of questions. It is even more tedious and difficult to evaluate portions of videos, where evaluation of a brief period of time from a video may be useful. Recommendations based on such a star rating are imprecise, subjective, and often unreliable.

SUMMARY

A computer implemented method is disclosed for affect based recommendations comprising: playing a first media presentation to an individual; capturing mental state data for the individual while the first media presentation is played; and recommending a second media presentation to the individual based on the mental state data for the individual which was captured. The method may further comprise analyzing the mental state data to produce mental state information. The method may further comprise correlating the mental state data which was captured for the individual to mental state data collected from other people who experienced the first media presentation. The recommending the second media presentation to the individual may be further based on the correlating between the individual and the other people. The first media presentation may include one of a group consisting of a movie, a television show, a web series, a webisode, a video, a video clip, an electronic game, an e-book, and an e-magazine. The second media presentation may include one of a group consisting of a movie, a television show, a web series, a webisode, a video, a video clip, an electronic game, an e-book, and an e-magazine. The first media presentation may be played on a web-enabled interface. The first media presentation may include one of a YouTube™, a Vimeo™ video, and a Netflix™ video. The second media presentation may include one of a YouTube™, a Vimeo™ video, and a Netflix™ video. The method may further comprise ranking the first media presentation relative to another media presentation based on the mental state data which was captured. The ranking may be for the individual based on the mental state data from the individual. The ranking may be based on anticipated preferences for the individual.

The mental state data may be captured from multiple people and further comprising aggregating the mental state data from the multiple people. The method may further comprise ranking the first media presentation relative to another media presentation based on the mental state data which was aggregated from the multiple people. The mental state data may include one of a group consisting of physiological data, facial data, and actigraphy data. The facial data may include information on one or more of a group consisting of facial expressions, action units, head gestures, smiles, brow furrows, squints, lowered eyebrows, raised eyebrows, smirks, and attention. The physiological data may include one or more of electrodermal activity, heart rate, heart rate variability, skin temperature, and respiration. The method may further comprise inferring of mental states based on the mental state data which was collected. The mental states may include one of a group consisting of frustration, confusion, disappointment, hesitation, cognitive overload, focusing, being engaged, attending, boredom, exploration, confidence, trust, delight, valence, skepticism, and satisfaction. The playing of the first media presentation may be done on a mobile device and further comprising recording of facial images with the mobile device as part of the capturing of the mental state data.

In embodiments, a computer program product embodied in a non-transitory computer readable medium may comprise: code for playing a first media presentation to an individual; code for capturing mental state data for the individual while the first media presentation is played; and code for recommending a second media presentation to the individual based on the mental state data for the individual which was captured. In some embodiments, a computer system for affect based recommendations may comprise: a memory for storing instructions; one or more processors attached to the memory wherein the one or more processors are configured to: play a first media presentation to an individual; capture mental state data for the individual while the first media presentation is played; and recommend a second media presentation to the individual based on the mental state data for the individual which was captured.

In some embodiments, a computer implemented method for affect based ranking may comprise: displaying a plurality of media presentations to a group of people; capturing mental state data from the group of people while the plurality of media presentations is displayed; correlating the mental state data captured from the group of people who viewed the plurality of media presentations; and ranking the media presentations relative to one another based on the mental state data. The method may further comprise tagging the plurality of media presentations with mental state information based on the mental state data which was captured.

Various features, aspects, and advantages of numerous embodiments will become more apparent from the following description.

BRIEF DESCRIPTION OF THE DRAWINGS

The following detailed description of certain embodiments may be understood by reference to the following figures wherein.

DETAILED DESCRIPTION

The present disclosure provides a description of various methods and systems for analyzing people's mental states as they view videos. The ability to properly evaluate people's response to videos enables accurate recommendation of other videos. These videos can be for any purpose, including, but not limited to, entertainment, education, or general information. Evaluation of mental states in response to videos provides unmatched insight into people's true reactions to these videos. A mental state may be an emotional state or a cognitive state. Examples of emotional states include happiness or sadness. Examples of cognitive states include concentration or confusion. Observing, capturing, and analyzing these mental states can yield significant information about people's reactions to a videos. Some terms commonly used in evaluation of mental states are arousal and/or valence. Arousal is an indication on the amount of activation or excitement of a person. Valence is an indication on whether a person is positively or negatively disposed. Affect may include analysis of arousal and valence. Affect may also include facial analysis for expressions such as smiles or brow furrowing. Analysis may be as simple as tracking when someone smiles or when someone frowns while viewing a video. Recommendations for other videos may, in some embodiments, be made based on tracking when someone smiles while watching one or more videos and recommending videos with similarities to those which made the individual smile.

Figure 1:
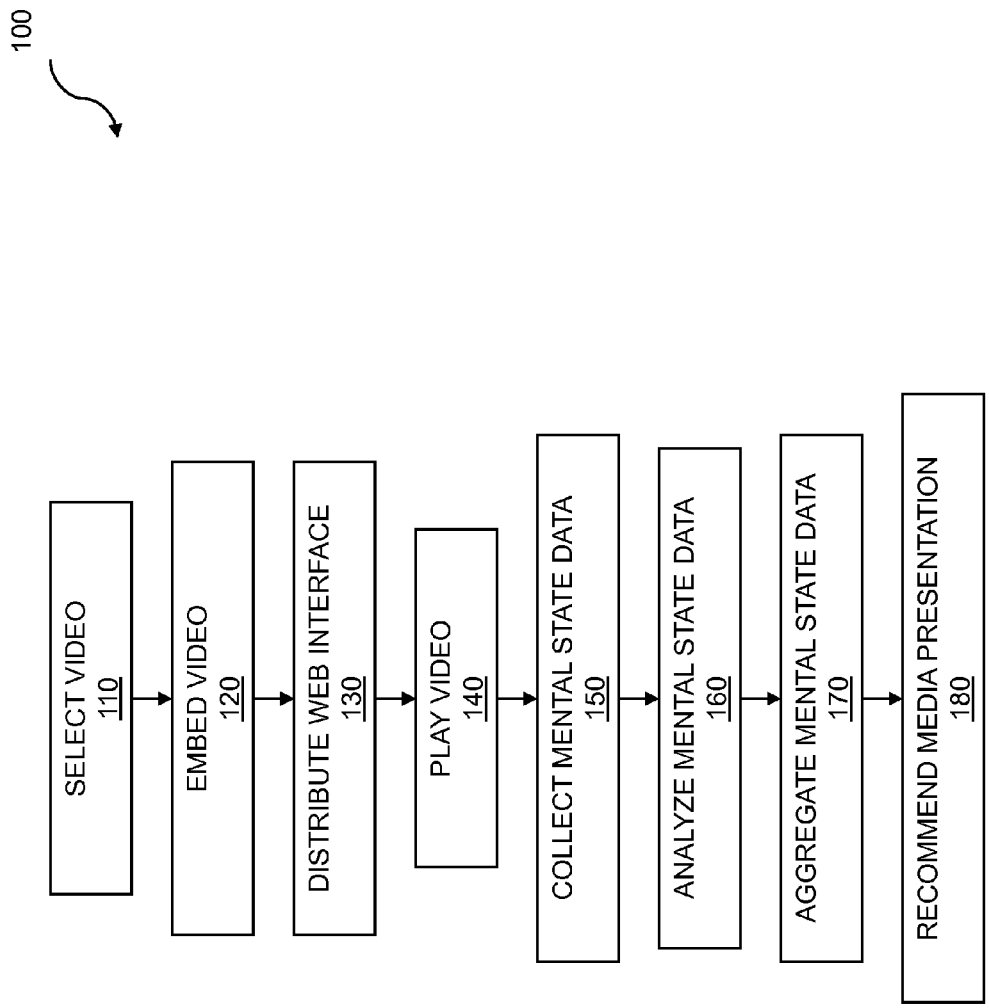
FIG. 1 is a flow diagram for displaying a video.

FIG. 1 is a flow diagram for displaying a video. A flow 100 is given for a computer-implemented method for rendering video. The flow 100 may begin with selecting a video 110. The video may be selected by a system which is automating the collection of affect on numerous videos. In embodiments, the video may be selected by a person who wants affect collected on the video. The video may include one of a YouTube™ and a Vimeo™ video. The flow 100 may continue with embedding the video 120 within a web-enabled interface wherein the web-enabled interface activates collecting of mental state data. The web-enabled interface may include a web page, web application, or the like. The embedding 120 may include inserting a link for the video into a URL on a web page that activates affect collection. The embedding 120 may include providing a link where a user can insert their own video. The affect may be collected by evaluating facial expressions. The evaluating facial expressions may include evaluating smiles or brow furrows. The affect may include evaluation of one of a group consisting of attention, engagement, interest, liking, and disliking The affect may be collected by evaluating physiology.

The flow 100 continues with distributing the web-enabled interface 130. The distributing of the web-enabled interface may include sending a URL. The sending of the URL may be accomplished using one of a group consisting of an email, a text message, a Facebook™ posting, a Twitter™ message, a Google+™ posting, a LinkedIn™ posting, a social network update, and a blog entry. In some embodiments, the sending may be accomplished by pressing or selecting a button on a web page associated with a video. Selecting the button may distribute the video. In some embodiments, selecting the button may also distribute mental state data or analysis of mental state data along with the video. The flow 100 may further comprise playing of the video 140, perhaps in the web-enabled interface, and collecting the mental state data 150 while the video is being played. The mental state data may be collected for a group of people who view the video.

The mental state data collected may include one of a group consisting of physiological data, facial data, and actigraphy data. The physiological data may include one or more of electrodermal activity, heart rate, heart rate variability, skin temperature, and respiration. The facial data may include information on one or more of a group consisting of facial expressions, action units, head gestures, smiles, brow furrows, squints, lowered eyebrows, attention, and the like. The mental states that may be inferred may include one of a group consisting of frustration, confusion, disappointment, hesitation, cognitive overload, focusing, being engaged, attending, boredom, exploration, confidence, trust, delight, frustration, valence, skepticism, and so on. The mental state data may be collected for an individual. Likewise, the mental state data may be captured from multiple people.

The flow 100 may continue with analyzing mental state data 160. The mental state data may be analyzed 160 to produce mental state information. Mental states for a viewer or a plurality of viewers may be inferred based on the mental state data which was collected.

The flow 100 may continue with aggregating mental state data 170. Mental state data may be collected from multiple people who view a video, and the mental state data from the multiple people may be aggregated. Thus, the mental state data is aggregated across a group of people. Results from the aggregating 170 may be presented as part of the displaying of a graphical representation.

The flow 100 may further comprise recommending a media presentation 180. The aggregating of the mental state data 170 may be used as part of the input to result in recommending a media presentation 180 to an individual based on the mental state data which was aggregated. The media presentation may be one of a group consisting of a movie, a television show, a web series, a webisode, a video, a video clip, an electronic game, an advertisement, an e-book, and an e-magazine. The flow 100 may further comprise recommending a media presentation to a second person based on the mental state data collected from a first person. Various steps in the flow 100 may be changed in order, repeated, omitted, or the like without departing from the disclosed inventive concepts. Various embodiments of the flow 100 may be included in a computer program product embodied in a non-transitory computer readable medium that includes code executable by one or more processors. The flow 100 may include tagging the plurality of media presentations with mental state information based on the mental state data which was captured.

Figure 2:
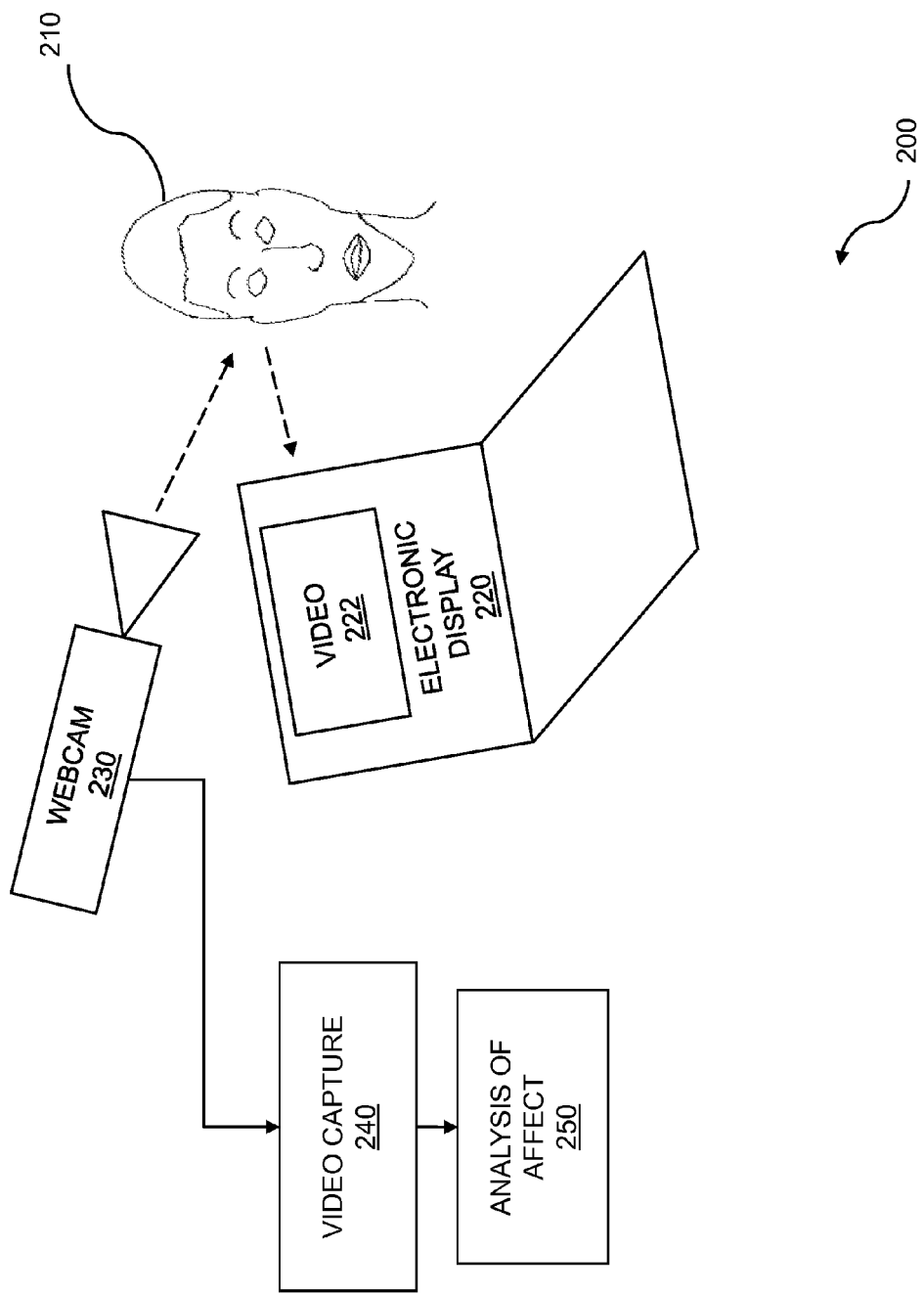
FIG. 2 is a system for capturing facial response to a video.

FIG. 2 is a system for capturing facial response to a video. A system 200 includes an electronic display 220 and a webcam 230. The system 200 captures facial response to a video 222 shown on the electronic display 220. The facial data may include video and collection of information relating to mental states. The facial data may include information on one or more of a group consisting of facial expressions, action units, head gestures, smile, brow furrows, squints, lowered eyebrows, raised eyebrows, smirks, and attention. In some embodiments, a webcam 230 may capture video of the person 210. Images of the person 210 may also be captured by a camera on a computer (such as a laptop, a net-book, a tablet, or the like), a video camera, a still camera, a cell phone camera, a mobile device camera (including, but not limited to, a forward facing camera), a thermal imager, a CCD device, a three-dimensional camera, a depth camera, and multiple webcams used to capture different views of viewers or any other type of image capture apparatus that may allow image data captured to be used by an electronic system. The capture of the facial response of person 210 to video 222 shown on display 220 may include collection of mental state data. The capture of the facial response of person 210 to video 222 shown on display 220 may include capture of physiological data. The physiological data may include one or more of heart rate, heart rate variability, skin temperature, respiration, and the like.

The electronic display 220 may show a video. The video 222 may be shown on any electronic display, including but not limited to, a computer display, a laptop screen, a net-book screen, a tablet computer screen, a cell phone display, a mobile device display, a remote with a display, a television, a projector, or the like. The electronic display 220 may include connections to a keyboard, mouse, joystick, touchpad, wand, motion sensor, and other input means. The video 222 may be displayed within a webpage, a website, a web-enabled application, or the like. The images of the person 210 may be captured by a video capture unit 240. In some embodiments, video of the person 210 is captured while in others a series of still images are captured.

Analysis of action units, gestures, mental states, and physiological data may be accomplished using the captured images of the person 210. The action units may be used to identify smiles, frowns, and other facial indicators of mental states. The gestures, including head gestures, may indicate interest or curiosity. For example, a head gesture of moving toward the video 222 may indicate increased interest or a desire for clarification. Based on the captured images, analysis of physiology may be performed. Analysis of affect 250 may be performed based on the information and images which are captured. The analysis can include facial analysis and analysis of head gestures. The analysis can include evaluating physiology and may include evaluating one of a group consisting of heart rate, heart rate variability, respiration, perspiration, temperature, and other bodily evaluation.

Figure 3:
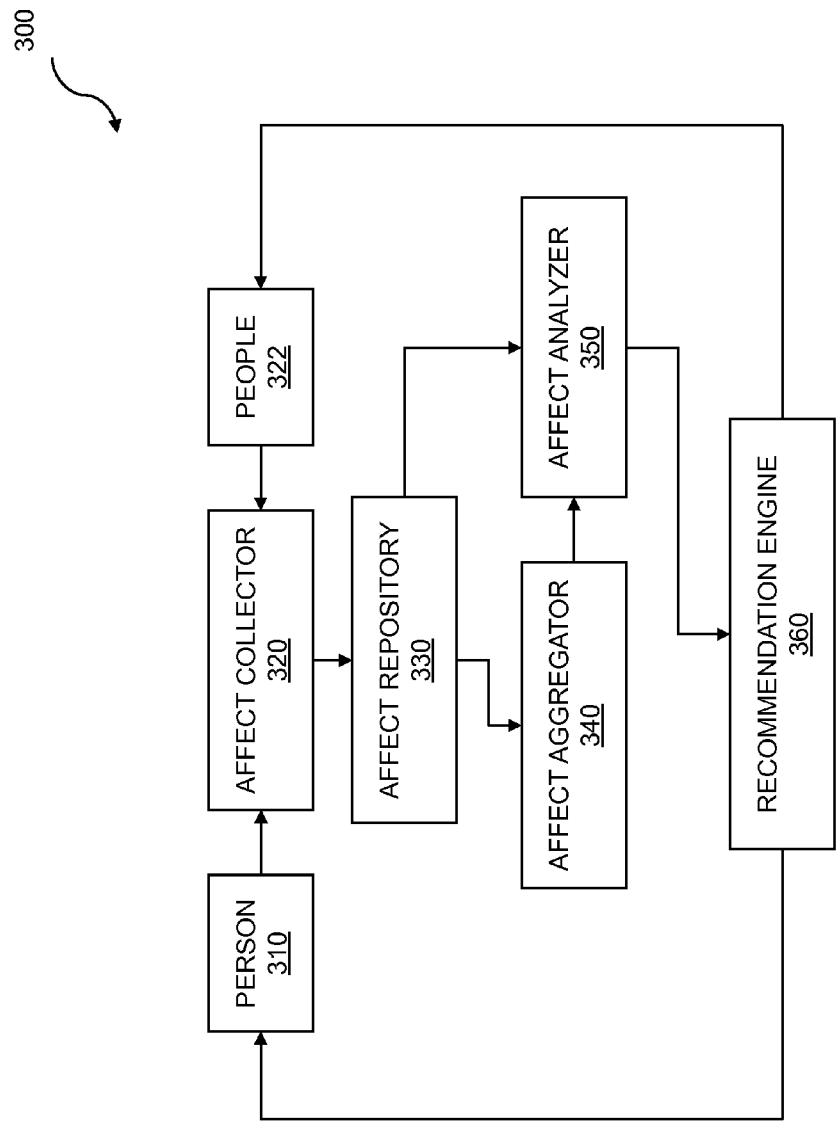
FIG. 3 is a diagram of a recommendation system.

FIG. 3 is a diagram of a recommendation system. A person 310 may view a video. While the person 310 is viewing a video, an affect collector 320 may gather affect data on the person 310. The affect collector 320 may be a webcam or other camera device. The affect collector 320 may be a biosensor attached to the person 310 in one or more locations. The affect data collected from the person 310 by the affect collector 320 can be stored in an affect repository 330. The affect repository 330 may be on a local computer or on a remote server, or may be distributed or part of a cloud computing system.

An affect analyzer 350 may analyze the affect data collected from the person 310. The affect analyzer 350 may recognize mental states including information on concentration, liking, disliking, etc. The affect analyzer 350 may recognize smiles or frowns. Based on the analysis done by the affect analyzer 350 a recommendation engine 360 may recommend a video or other media presentation to the person 310. The recommending of a media presentation to an individual may be based on the mental state data which was aggregated. The aggregated data may be for multiple videos by an individual or may be for a plurality of people. The recommendation may be based on common factors with one or more videos which the person 310 watched. For example, if the person 310 smiled for each of the videos that he or she watched with a specific actress as the main character, then the recommendation engine 360 may recommend another video with the same actress to the person 310. In another example, if a series of sports videos is liked by the person 310 then another sports video may be recommended.

Other people 322 may view the same video as the person 310. In some embodiments, multiple videos are viewed by the person 310 and the other people 322. In embodiments, different subsets of the multiple videos are viewed by each person. The affect collector 320 may capture affect data for each of the people 322. The affect collector 320 may be a single unit such as a kiosk in a mall or a device which collects affect for multiple people viewing a video in such a location as a conference room or a movie theater. Alternatively the affect collector 320 may be separate devices such as in the case where each person has their own computer, laptop, cell phone, mobile device, or the like. The affect repository 330 may retain affect data from the people on whom affect data is collected.

An affect aggregator 340 may take affect data from the affect repository and correlate affect data from the person 310 with the other people 322. The affect aggregator 340 may recognize trends for the person 310 who has watched multiple videos, or, for example, movies. The affect aggregator 340 may determine correlation vectors for the person 310 and the people 322 or a subset thereof. A correlation may be made using weighted Euclidean or Mahalanobis distance evaluation between two vectors, where a vector includes an individual's affect data. There are many ways to compute distances or similarity/dissimilarity measures. Collaborative filtering or the like may be used to aid in matching affect data between or among people. In some embodiments, a comparison is made based on the same content viewed by the person 310 and by individuals from the other people 322. When one vector is at a sufficiently small distance from another person's vector then the affect aggregator 340 will look for other content that has been liked or smiled at. This other content may be recommended by the recommendation engine 360 to the person 310 because there are assumed similarities based on the affect data which was collected.

In some embodiments, the affect aggregator 340 and affect analyzer 350 may be used to review affect data stored in the affect repository to compare affect data collected on a new video with an historical database of affect data for videos. The new video may be evaluated to determine how this video ranks against other videos. For example, the new video could be compared with a "top 100" list of videos to determine the relative number of smiles that the new video has relative to the "top 100" list of videos for which people smiled. In embodiments, a group of people can view a new video and have affect data collected. The affect data collected for the people could be aggregated together. The aggregated affect data for the new video could then be compared to the aggregated affect data for other videos. This type of comparison could be used by developers of videos to rank and evaluate a new video which has been produced. Likewise a buyer of advertising spots, for example, could evaluate a new video based on aggregated affect data collected from a group of people. For certain purposes an emotion profile could be generated and then compared with a "best of breed" set of videos by network studios, advertisers, or others with similar commercial interest.

In some cases there may be good correlation for one type of video but not another. For instance, a good correlation may be made for drama videos but a poor one for comedy video. Based on that information, a recommendation may be made for another drama video. Collaborative filtering may be performed to identify good possibilities for correlation and therefore areas where videos may be recommended.

The recommendation engine 360 may make recommendations to the person 310 on whom affect was collected. The recommendation engine 360 may make these recommendations based on the correlation between the person 310 and the other people 322. Likewise, the recommendation engine 360 may make recommendations to one or more of the people 322 based on a video that was viewed by the person 310.

Figure 4:
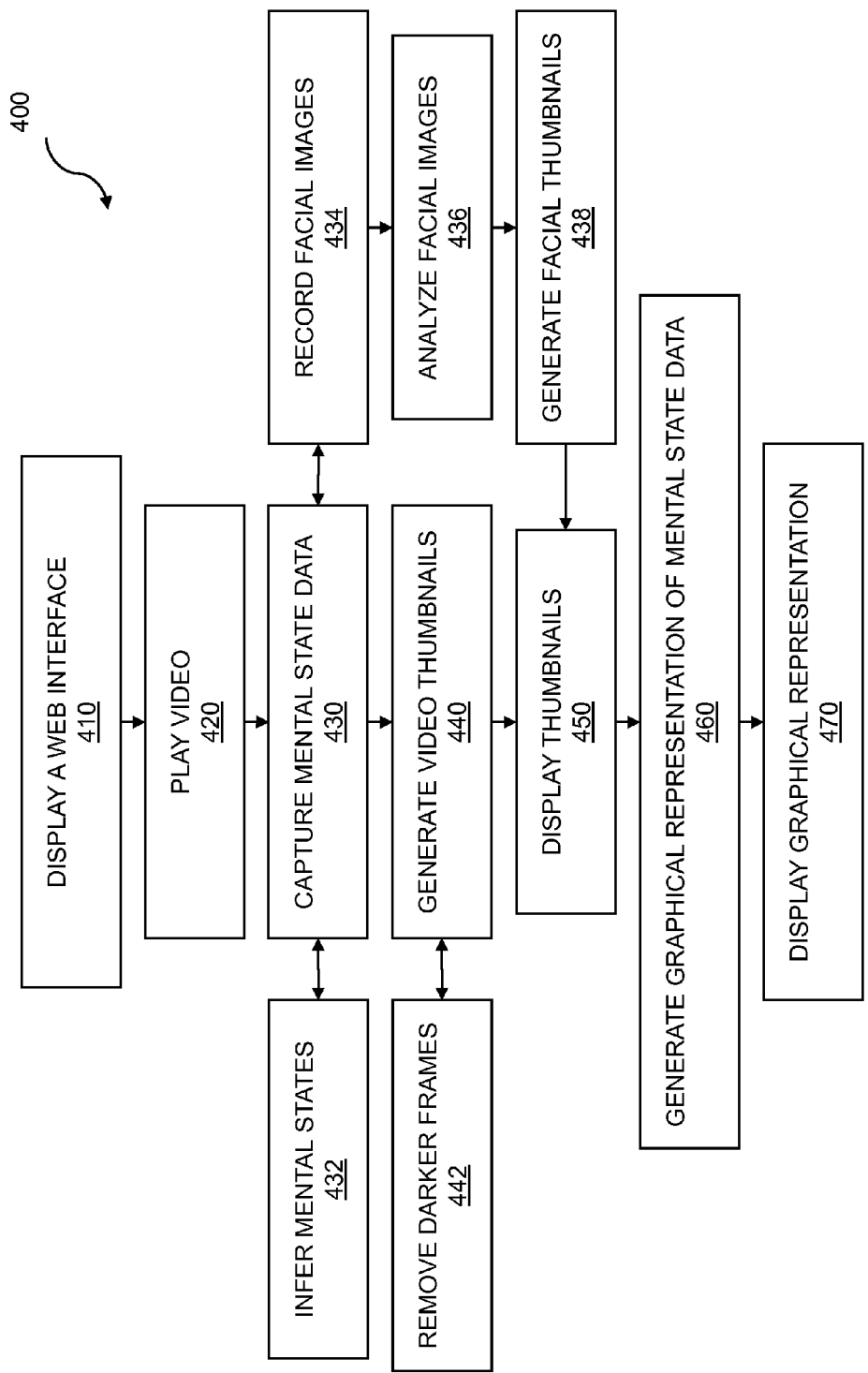
FIG. 4 is a flow diagram for displaying affect.

FIG. 4 is a flow diagram for displaying affect. The flow 400 describes a computer-implemented method for displaying affect. The flow 400 may begin with displaying a first web-enabled interface 410. The first web-enabled interface may include a web page. The flow 400 may continue with playing a video 420 on the first web-enabled interface. The video may include a YouTube™ or a Vimeo™ video. The video may be one of a group consisting of a movie, a television show, a web series, a webisode, a video, a video clip, or may be media such as an electronic game, an advertisement, an e-book, an e-magazine, or a movie trailer. The flow 400 may continue with capturing mental state data 430 while the video is played. The flow may further comprise inferring of mental states 432 based on the mental state data which was collected. The mental states may include one of a group consisting of frustration, confusion, disappointment, hesitation cognitive overload, focusing, being engaged, attending, boredom, exploration, confidence, trust, delight, valence, skepticism, and satisfaction.

The capturing mental state data may further comprise recording facial images 434. The flow 400 may further comprise analyzing the facial images for a facial expression 436. The facial data may include information on one or more of a group consisting of facial expressions, action units, head gestures, smiles, brow furrows, squints, lowered eyebrows, raised eyebrows, smirks, attention, and the like. The facial expressions may be used to generate facial thumbnails 438. In some embodiments, representative low-resolution images may be included in the thumbnails rather than images obtained directly from a webcam or other imaging apparatus.

The flow 400 may continue with generating a set of thumbnails 440 for the video which was played, where the thumbnails comprise scenes from the video and the set of thumbnails may be generated automatically. The flow 400 may further comprise analyzing the set of thumbnails and removing a frame from the set of thumbnails based on a dark threshold. Another frame may be used in place of the frame that was removed. The flow 400 may continue with displaying the set of thumbnails 450 on a second web-enabled interface. The second web-enabled interface may include a web page. In embodiments, the thumbnails will be for the video which was played.

In embodiments, an individual thumbnail is one "scene" from the video and is a static image of a specified size. Various items can be useful in the generation of thumbnails and are briefly discussed here. A composite of thumbnails or zoetrope is a horizontal array of images. A dark threshold is used to analyze a mean value of the color of an image to determine whether it is "dark." A starting offset is a number of seconds into the video to begin the thumbnail generation process. A number of seconds between frames can be automatically generated or specified manually and refers to the number of seconds between the individual thumbnail images. A zoetrope width is the width of the final image and may be slightly different from the width of an individual thumbnail multiplied by the number of thumbnails. A size string may be of the form "width times height" and examples include 24×24, 32×32, 40×32, etc. The size string determines the dimensions of the individual thumbnail. The individual thumbnails may be examined to determine if the image is "too dark." Some movie trailers frequently fade to black. Black or very dark frames often make for poor thumbnails. A recursive look forward and backward to find a better frame is possible. If a frame is too dark, then the recursive algorithm looks behind and forward by small amounts to see if it can find a better frame that can be found within certain recursion limits. Once a good image is found or a recursion limit is reached, the video is advanced by the appropriate number of seconds between frames to identify the next thumbnail image.

In some embodiments, the flow 400 may further comprise generating a set of thumbnails for the facial images which were recorded 438 and displaying the set of thumbnails 450 for the facial images on the second web-enabled interface. One thumbnail from the set of thumbnails may be selected based on a facial expression. The one thumbnail may show an animated facial expression. The one thumbnail may show an unusual facial expression. The one thumbnail may show a typical facial expression.

The flow 400 may continue with generating a graphical representation of the mental state data 460 which was captured. The graphical representation may be a line graph showing an amount of a specific mental state or an amount of a specific facial expression. Likewise the graphical representation may be a more complex dashboard-type presentation. The flow 400 may continue with displaying the graphical representation 470 on the second web-enabled interface. The graphical representation may include a score representing the mental state data. The score may be for a specific mental state, such as attention, frustration, disappointment, or any other mental state. The score may provide a numerical representation of the mental state.

In some embodiments, the playing of the video is done on a mobile device and the recording of the facial images is done with the mobile device. In embodiments, the mental state data is captured from multiple people and aggregated. Various steps in the flow 400 may be changed in order, repeated, omitted, or the like without departing from the disclosed inventive concepts. Various embodiments of the flow 400 may be included in a computer program product embodied in a non-transitory computer readable medium that includes code executable by one or more processors.

Figure 5:
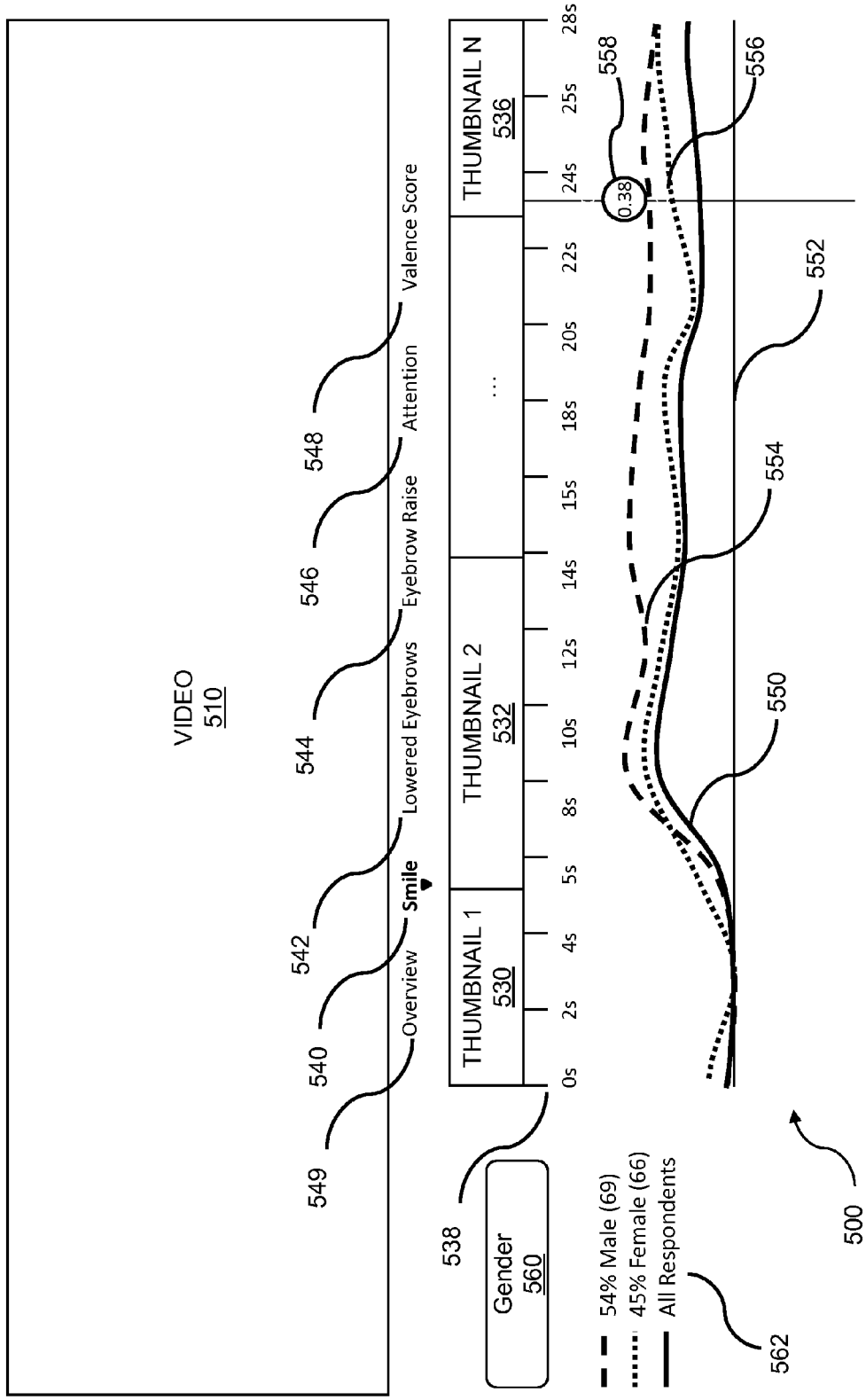
FIG. 5 is a graphical representation of displaying affect.

FIG. 5 is a graphical representation of displaying affect. Display, or dashboard, 500 is a graphical representation of mental state analysis that may be shown for video viewer analysis and may be presented on an electronic display. The display may be a television monitor, projector, computer monitor (including a laptop screen, a tablet screen, a net-book screen, and the like), a cell phone display, a mobile device, or other electronic display. In embodiments, the display may be a webpage. An example window 500 is shown which includes, for example, a rendering of a video 510 along with associated mental state information. The visualization may further comprise the rendering related to the video 510. A user may be able to select among a plurality of video renderings using various buttons and/or tabs. The user interface allows a plurality of parameters to be displayed as a function of time, synchronized to the video rendering 510. Various embodiments may have any number of selections available for the user, and some may include other types of renderings instead of video. A set of thumbnail images for the selected rendering, that in the example shown, include Thumbnail 1 530, Thumbnail 2 532, through Thumbnail N 536 which may be shown below the rendering along with a timeline 538. The thumbnails may show a graphic "storyboard" of the video rendering. This storyboard may assist a user in identifying a particular scene or location within the video rendering. Some embodiments may not include thumbnails, or may have a single thumbnail associated with the rendering, while various embodiments may have thumbnails of equal length and others may have thumbnails of differing lengths. In some embodiments, the start and/or end of the thumbnails may be determined based on changes in the captured viewer mental states associated with the rendering, or may be based on particular points of interest in the video rendering. Thumbnails of one or more viewers may be shown along the timeline 538. The thumbnails of viewers may include peak expressions, expressions at key points in the video rendering 510, etc.

Some embodiments may include the ability for a user to select a particular type of mental state information for display using various buttons or other selection methods. The mental state information may be based on one or more descriptors. The one or more descriptors may include, but are not limited to, one of action unit 4 (AU4), action unit 12 (AU12), and valence. By way of example, in the window 500, the smile mental state information is shown as the user may have previously selected the Smile button 540. Other types of mental state information that may be available for user selection in various embodiments may include the Lowered Eyebrows button 542, Eyebrow Raise button 544, Attention button 546, Valence Score button 548, or other types of mental state information, depending on the embodiment. An Overview button 549 may be available to allow a user to show graphs of the multiple types of mental state information simultaneously. The mental state information may include probability information for one or more descriptors, and the probabilities for the one of the one or more descriptors may vary for portions of the video rendering.

Because the Smile option 540 has been selected in the example shown, smile graph 550 may be shown against a baseline 552, showing the aggregated smile mental state information of the plurality of individuals from whom mental state data was collected for the video. The male smile graph 554 and the female smile graph 556 may be shown so that the visual representation displays the aggregated mental state information. These graphs are provided by way of example only. The mental state information may be based on a demographic basis as those viewers who comprise that demographic react to the video. The various demographic based graphs may be indicated using various line types as shown or may be indicated using color or other method of differentiation. A slider 558 may allow a user to select a particular time of the timeline and show the value of the chosen mental state for that particular time. The video 510 may be coordinated with the slider 558. The slider 558 may be selected and moved with a mouse or other pointing device in some embodiments. The video 510 may jump to the point in time to which the slider 558 has been moved. The mental states can be used to evaluate the value of the video.

Various types of demographic-based mental state information may be selected using the demographic button 560 in some embodiments. Such demographics may include gender, age, race, income level, education, or any other type of demographic including dividing the respondents into those respondents that had higher reactions from those with lower reactions. A graph legend 562 may be displayed indicating the various demographic groups, the line type or color for each group, the percentage of total respondents and/or absolute number of respondents for each group, and/or other information about the demographic groups. The mental state information may be aggregated according to the demographic type selected. Thus, aggregation of the mental state information is performed on a demographic basis so that mental state information is grouped based on the demographic basis, for some embodiments. The video thus may be evaluated for responses by various demographic groups.

Figure 6:
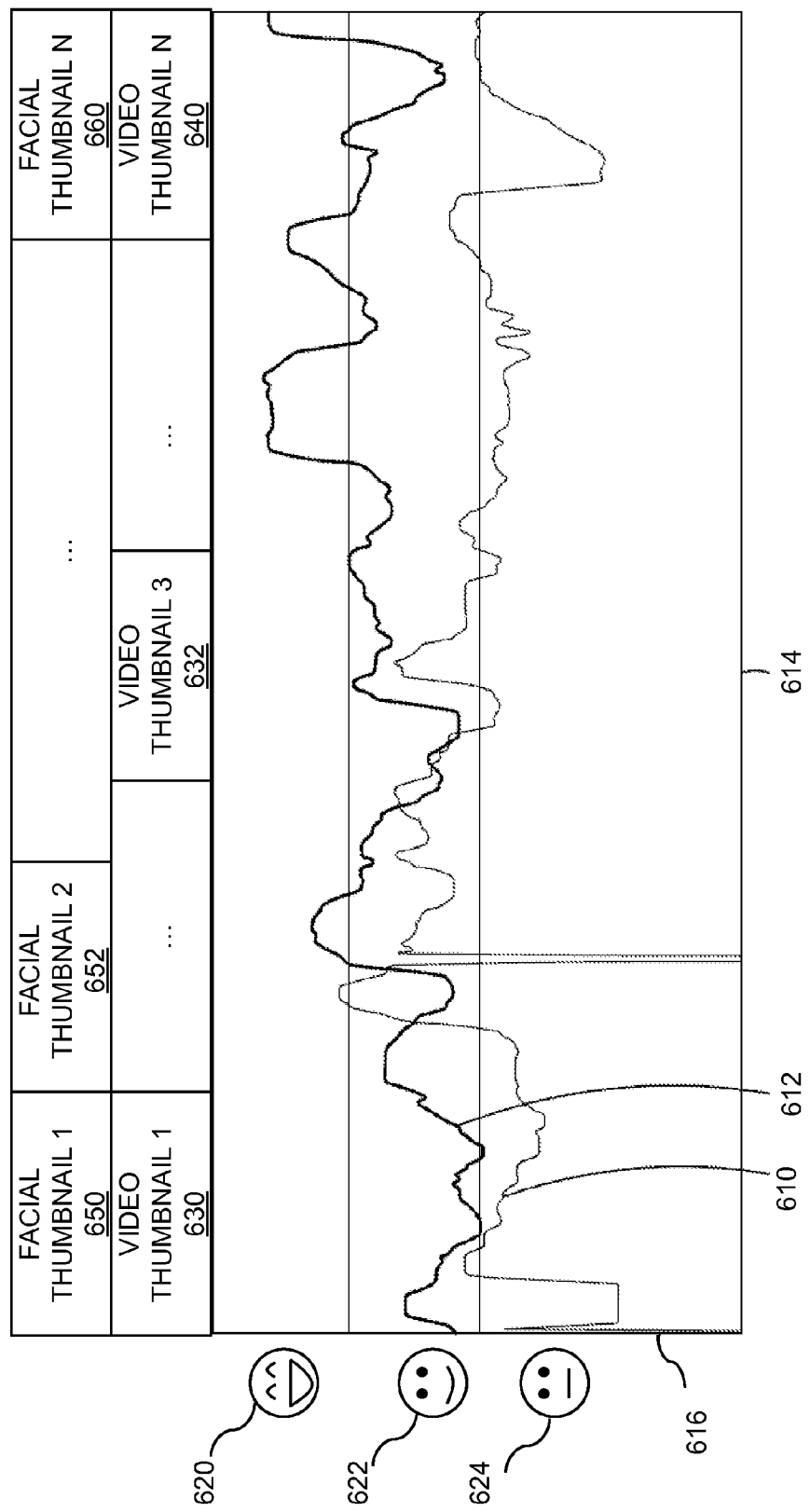
FIG. 6 is a graphical representation for displaying aggregated affect.

FIG. 6 is a graphical representation for displaying affect based on mental state analysis along with an aggregated result from a group of people. This rendering may be displayed on a web page, web enabled application, a dashboard, or other type of electronic display representation. A graph 610 may be shown for an individual on whom affect data is collected. Another graph 612 may be shown for affect collected on another individual or aggregated affect from multiple people. The mental state analysis may be based on facial image or physiological data collection. In some embodiments, the graph 610 may indicate the amount or probability of a smile being observed for the individual. A higher value or point on the graph may indicate a stronger or larger smile. In certain spots the graph may drop out or degrade when image collection was lost or was not able to identify the face of the person. The probability or intensity of an affect may be given along the y-axis 616. A timeline may be given along the x-axis 614. The aggregated information may be based on taking the average, median, or other statistical or calculated value based on the information collected from a group of people. In some embodiments, combination of the aggregated mental state information is accomplished using computational aggregation.

In some embodiments, graphical smiley face icons 620, 622, and 624 may be shown providing an indication of the amount of a smile or other facial expression. A first very broad smiley face icon 620 may indicate a very large smile being observed. A second normal smiley face icon 622 may indicate a smile being observed. A third face icon 624 may indicate no smile. The icons may correspond to a region on the y-axis 616 that indicate the probability or intensity of a smile.

A set of facial thumbnail images related to the selected graph or graphs, that in the example shown, include Facial Thumbnail 1 650, Facial Thumbnail 2 652, through Facial Thumbnail N 660, may be shown above or below the graph, and may be displayed with a timeline or other parameter along the x-axis 614. The thumbnails may show a graphic "storyboard" of the facial rendering. This storyboard may assist a user in identifying a particular scene or location within the facial rendering. Some embodiments may not include thumbnails, or may have a single thumbnail associated with the facial rendering, while various embodiments may have thumbnails of equal length while others may have thumbnails of differing lengths. In some embodiments, the start and/or end of the thumbnails may be determined based on changes in the captured viewer mental states associated with the rendering, or may be based on particular points of interest in the video rendering. Thumbnails of one or more viewers may be shown along a timeline or other parameter 614. The thumbnails of viewers may include peak expressions, expressions at key points in the video rendering, key points in the graphs, etc.

A set of video thumbnail images comprising scenes from the video for the selected graph or graphs, that in the example shown, include Video Thumbnail 1 630, Video Thumbnail 2 632, through Video Thumbnail N 640, may be shown above or below the graph, and may be displayed with a timeline or other parameter along the x-axis 614. The thumbnails may show a graphic "storyboard" of the video rendering. This storyboard may assist a user in identifying a particular scene or location within the video rendering. Some embodiments may not include thumbnails, or may have a single thumbnail associated with the rendering, while various embodiments may have thumbnails of equal length while others may have thumbnails of differing lengths. In some embodiments, the start and/or end of the thumbnails may be determined based on changes in the captured viewer mental states associated with the rendering, or may be based on particular points of interest in the video rendering.

Figure 7:
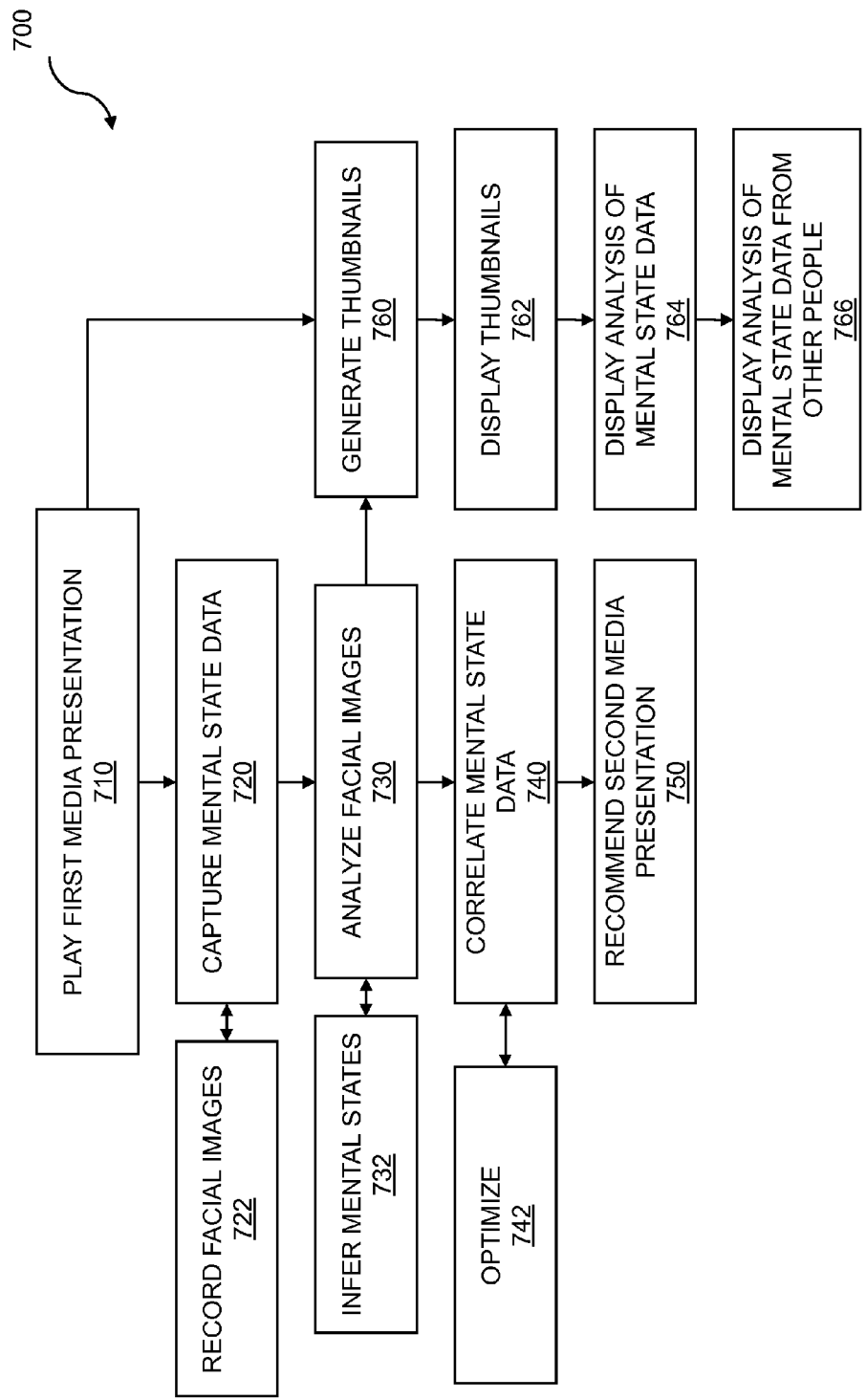
FIG. 7 is a flow diagram for affect-based recommendations.

FIG. 7 is a flow diagram for affect-based recommendations. A flow 700 describes a computer-implemented method for affect-based recommendations. The flow 700 may begin with playing a first media presentation 710 to an individual. The first media presentation may be one of a group consisting of a movie, a television show, a web series, a webisode, a video, a video clip, an electronic game, an e-book, and an e-magazine, or other media object. The first media presentation may include a YouTube™ video, a Vimeo™ video, or a Netflix™ video. The first media presentation may be played on a web-enabled interface or other electronic display interface. The web-enabled interface may include a web page. The playing of the first media presentation may be done on a mobile device. The flow 710 may continue with capturing mental state data 720 for the individual while the first media presentation is played. The mental state data collected may include physiological data, facial data, actigraphy data, and the like. The capturing of mental state data may further comprise recording facial images 722. Capture of the facial image may be realized by a webcam or other camera. The playing of the first media presentation may be done on a mobile device and the recording of the facial images may also be done with the mobile device. The recording of facial images 722 with the mobile device may be part of the capturing of mental state data. The flow 700 may further comprise analyzing the facial images 730 for a facial expression. The facial expression may include a smile. The facial expression may include a brow furrow. The analyzing facial images may further comprise using the facial images to infer mental states 732. The mental states may include frustration, confusion, disappointment, hesitation, cognitive overload, focusing, being engaged, attending, boredom, exploration, confidence, trust, delight, satisfaction, valence, skepticism, happiness, and the like.

The flow 700 may continue with correlating the mental state data 740 which was captured for the individual to mental state data collected from other people who experienced the first media presentation. The correlating may include identifying similar likes and dislikes as well as similar various other mental states. In some embodiments, distributions of responses to various videos may be correlated. In other embodiments, differences may be correlated, such as, for example, identifying maximally dissimilar responses. In some embodiments, certain mental states may be identified as being similar while others are identified as being dissimilar during part of the correlation. The flow 700 may include optimizing 742 the media presentation based on the mental state data. The optimizing 742 may include modifying content or recommending changes in content, such as eliminating scenes, reducing certain material, or emphasizing certain actors. In embodiments, the media presentation includes a mixture of advertizing and content. The optimizing 742 may select one or more advertisements to be interspersed with the content. The optimizing 742 may include ordering one or more advertisements to be interspersed with the content. The optimizing 742 may include selecting times within the content for playing the one or more advertisements. The optimizing 742 may include identifying portions of an advertisement that are removed to form a shortened advertisement.

The flow 700 may include recommending a second media presentation 750 to the individual based on the mental state data which was captured for the individual. The recommending the second media presentation to the individual may be based on the correlating between the individual and the other people. The second media presentation may be one of a group consisting of a movie, a television show, a web series, a webisode, a video, a video clip, an electronic game, an e-book, and an e-magazine, and the like. The second media presentation may include a YouTube™ video, a Vimeo™ video, or a Netflix™ video.

The flow 700 may further comprise generating a set of thumbnails 760 for the first media presentation which was played and displaying the set of thumbnails 762 on a second web-enabled interface or digital display along with an analysis of the mental state data from the individual 764. The set of thumbnails may comprise scenes from the first media presentation. The selection of the thumbnail from the set of thumbnails may be based on facial expression. The set of thumbnails may be generated automatically and may include removing a frame from the set of thumbnails based on a dark threshold. Another frame may be used in place of the frame that was removed. The flow 700 may further comprise displaying an analysis of the mental state data from the other people 766. Various steps in the flow 700 may be changed in order, repeated, omitted, or the like without departing from the disclosed inventive concepts. Various embodiments of the flow 700 may be included in a computer program product embodied in a non-transitory computer readable medium that includes code executable by one or more processors.

Figure 8:
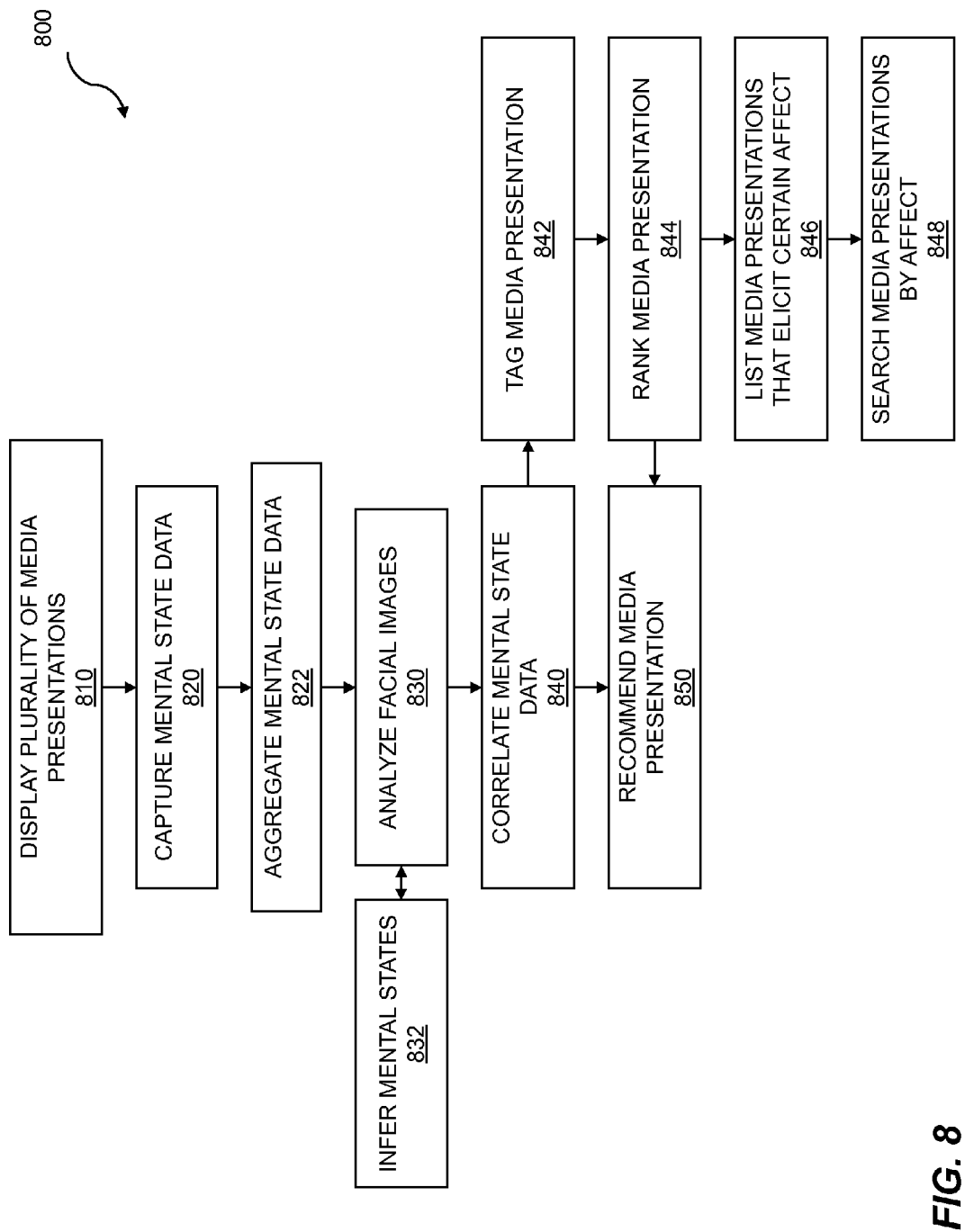
FIG. 8 is a flow diagram for affect-based video ranking

FIG. 8 is a flow diagram for affect-based video ranking and includes a flow 800 which describes a computer-implemented method for affect-based ranking The flow 800 may begin with displaying a plurality of media presentations 810 to a group of people. The plurality of media presentations may include videos. The plurality of videos may include YouTube™ videos, Vimeo™ videos, or Netflix™ videos. Further, the plurality of media presentations may include one of a group consisting of a movie, a movie trailer, a television show, a web series, a webisode, a video, a video clip, an advertisement, a music video, an electronic game, an e-book, and an e-magazine. The flow 800 may continue with capturing mental state data 820 from the group of people while the plurality of media presentations is displayed. Thus, mental state data may be captured from multiple people. The affect data may include facial images. In some embodiments, the playing of the media presentations is done on a mobile device and the recording of the facial images is done with the mobile device. The flow 800 may include aggregating the mental state data 822 from the multiple people. The flow 800 may further comprise analyzing the facial images 830 for a facial expression. The facial expression may include a smile. The facial expression may include a brow furrow. The flow 800 may further comprise using the facial images to infer mental states 832. The mental states may include one of a group consisting of frustration, confusion, disappointment, hesitation, cognitive overload, focusing, being engaged, attending, boredom, exploration, confidence, trust, delight, valence, skepticism, satisfaction, and the like.

The flow 800 may include correlating the mental state data 840 captured from the group of people who have viewed the plurality of media presentations and had their mental state data captured. The plurality of videos viewed by the group of people may have some common videos seen by each of the people in the group of people. In some embodiments, the plurality of videos may not include an identical set of videos. The flow 800 may continue with tagging the plurality of media presentations 842 with mental state information based on the mental state data which was captured. The affect information may simply be the affect data. In other embodiments, the affect information may be the inferred mental states. In still other embodiments the affect information may be results of the correlation. The flow 800 may continue with ranking the media presentations 844 relative to another media presentation based on the mental state data which was collected. The ranking may be for an individual based on the mental state data captured from the individual. The ranking may be based on anticipated preferences for the individual. In some embodiments, the ranking of a first media presentation relative to another media presentation may be based on the mental state data which was aggregated from multiple people. The ranking may also be relative to media presentations previously stored with affect information. The ranking may include ranking a video relative to another video based on the mental state data which was captured. The flow 800 may further comprise displaying the videos which elicit a certain affect 846. The certain affect may include one of a group consisting of smiles, engagement, attention, interest, sadness, liking, disliking, and so on. The ranking may further comprise displaying the videos which elicited a larger number of smiles. As a result of ranking, the media presentations may be sorted based on which are funniest, saddest, generate the most tears, or engender some other response. The flow 800 may further comprise searching through the videos based on a certain affect data 848. A search 848 may identify videos which are very engaging, funny, sad, poignant, or the like.

The flow 800 may include recommending a second media presentation 850 to an individual based on the affect data that was captured and based on the ranking The second media presentation may be one of a group consisting of a movie, a movie trailer, a television show, a web series, a webisode, a video, a video clip, an advertisement, a music video, an electronic game, an e-book, and an e-magazine.

Based on the mental states, recommendations to or from an individual may be provided. One or more recommendations may be made to the individual based on mental states, affect, or facial expressions. A correlation may be made between one individual and others with similar affect exhibited during multiple videos. The correlation may include a record of other videos, games, or other experiences along with their affect. Likewise a recommendation for a movie, video, video clip, webisode or other activity may be made to individual based on their affect. Various steps in the flow 800 may be changed in order, repeated, omitted, or the like without departing from the disclosed inventive concepts. Various embodiments of the flow 800 may be included in a computer program product embodied in a non-transitory computer readable medium that includes code executable by one or more processors.

Figure 9:
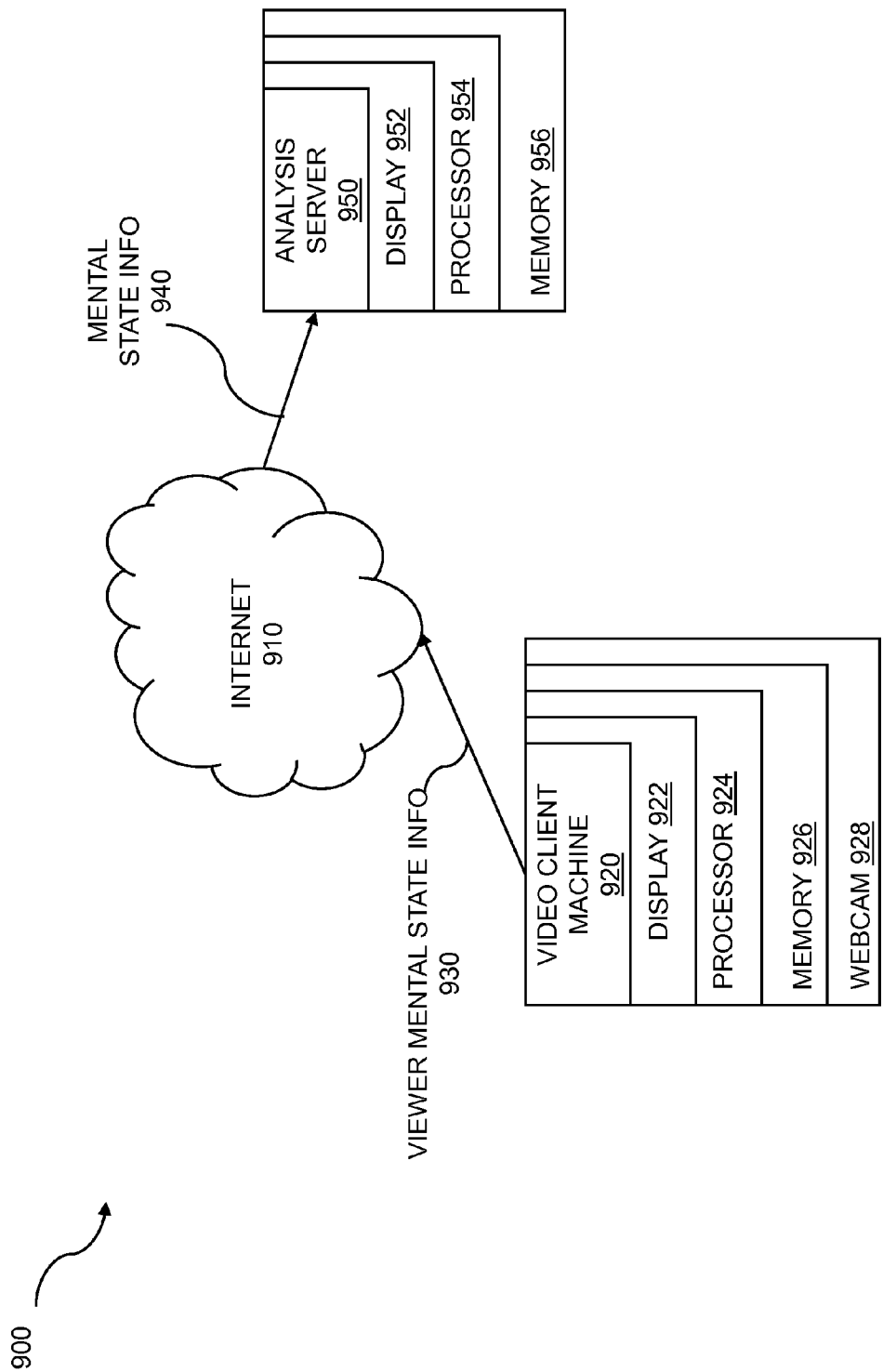
FIG. 9 is a system diagram for analyzing mental state information.

FIG. 9 is a system diagram for analyzing mental state information. The system 900 may include the Internet 910, intranet, or other computer network, which may be used for communication between or among the various computers of the system 900. A video client machine or client computer 920 has a memory 926 which stores instructions, and one or more processors 924 attached to the memory 926 wherein the one or more processors 924 can execute instructions stored in the memory 926. The memory 926 may be used for storing instructions, for storing mental state data, for system support, and the like. The client computer 920 also may have an Internet connection to carry viewer mental state information 930, and a display 922 that may present various videos to one or more viewers. The client computer 920 may be able to collect mental state data from one or more viewers as they observe the video or videos. In some embodiments there may be multiple client computers 920 that collect mental state data from viewers as they observe a video. The video client computer 920 may have a camera, such as a webcam 928, for capturing viewer interaction with a video including, in some embodiments, video of the viewer. The camera 928 may refer to a webcam, a camera on a computer (such as a laptop, a net-book, a tablet, or the like), a video camera, a still camera, a cell phone camera, a mobile device camera (including, but not limited to, a forward facing camera), a thermal imager, a CCD device, a three-dimensional camera, a depth camera, and multiple webcams used to capture different views of viewers or any other type of image capture apparatus that may allow image data captured to be used by the electronic system.

Once the mental state data has been collected, the client computer may upload information to a server or analysis computer 950, based on the mental state data from the plurality of viewers who observe the video. The client computer 920 may communicate with the server 950 over the Internet 910, intranet, some other computer network, or by any other method suitable for communication between two computers. In some embodiments, the analysis computer 950 functionality may be embodied in the client computer.

The analysis computer 950 may have a connection to the Internet 910 to enable mental state information 940 to be received by the analysis computer 950. Further, the analysis computer 950 may have a memory 956 which stores instructions, data, help information and the like, and one or more processors 954 attached to the memory 956 wherein the one or more processors 954 can execute instructions. The memory 956 may be used for storing instructions, for storing mental state data, for system support, and the like. The analysis computer 950 may use the Internet 910, or other computer communication method, to obtain mental state information 940. The analysis computer 950 may receive mental state information collected from a plurality of viewers from the client computer or computers 920, and may aggregate mental state information on the plurality of viewers who observe the video.

The analysis computer 950 may process mental state data or aggregated mental state data gathered from a viewer or a plurality of viewers to produce mental state information about the viewer or plurality of viewers. In some embodiments, the analysis server 950 may obtain mental state information 930 from the video client 920. In this case the mental state data captured by the video client 920 was analyzed by the video client 920 to produce mental state information for uploading. Based on the mental state information produced, the analysis server 950 may project a value based on the mental state information for one or more videos. The analysis computer 950 may also associate the aggregated mental state information with the rendering and also with the collection of norms for the context being measured.

In some embodiments, the analysis computer 950 may receive or provide aggregated mental state information based on the mental state data from the plurality of viewers who observe the video and may present aggregated mental state information in a rendering on a display 952. In some embodiments, the analysis computer may be set up for receiving mental state data collected from a plurality of viewers as they observe the video, in a real-time or near real-time embodiment. In at least one embodiment, a single computer may incorporate the client, server and analysis functionalities. Viewer mental state data may be collected from the client computer or computers 920 to form mental state information on the viewer or plurality of viewers viewing a video. The mental state information resulting from the analysis of the mental state date of a viewer or a plurality of viewers may be used to project a video value based on the mental state information. The system 900 may include computer program product embodied in a non-transitory computer readable medium comprising: code for playing a first media presentation to an individual, code for capturing mental state data for the individual while the first media presentation is played, and code for recommending a second media presentation to the individual based on the mental state data for the individual which was captured. The system 900 may include capabilities for affect-based recommendation comprising: a memory for storing instructions, one or more processors attached to the memory wherein the one or more processors are configured to play a first media presentation to an individual, capture mental state data for the individual while the first media presentation is played, and recommend a second media presentation to the individual based on the mental state data for the individual which was captured. The system 900 may include computer program product embodied in a non-transitory computer readable medium comprising: code for selecting a video; code for embedding the video within a web-enabled interface wherein the web-enabled interface activates collecting of mental state data; and code for distributing the web-enabled interface. The system 900 may include capabilities for rendering video comprising: a memory for storing instructions; one or more processors attached to the memory wherein the one or more processors are configured to: select a video; embed the video within a web-enabled interface wherein the web-enabled interface activates collecting of mental state data; and distribute the web-enabled interface.

The above methods may be executed on one or more processors on one or more computer systems. Embodiments may include various forms of distributed computing, client/server computing, and cloud based computing. Further, it will be understood that for the flow diagrams in this disclosure, the depicted steps or boxes are provided for purposes of illustration and explanation only. The steps may be modified, omitted, or re-ordered and other steps may be added without departing from the scope of this disclosure. Further, each step may contain one or more sub-steps. While the foregoing drawings and description set forth functional aspects of the disclosed systems, no particular arrangement of software and/or hardware for implementing these functional aspects should be inferred from these descriptions unless explicitly stated or otherwise clear from the context. All such arrangements of software and/or hardware are intended to fall within the scope of this disclosure.

The block diagrams and flow diagram illustrations depict methods, apparatus, systems, and computer program products. Each element of the block diagrams and flow diagram illustrations, as well as each respective combination of elements in the block diagrams and flow diagram illustrations, illustrates a function, step or group of steps of the methods, apparatus, systems, computer program products and/or computer-implemented methods. Any and all such functions may be implemented by computer program instructions, by special-purpose hardware-based computer systems, by combinations of special purpose hardware and computer instructions, by combinations of general purpose hardware and computer instructions, by a computer system, and so on. Any and all of which may be generally referred to herein as a "circuit," "module," or "system."

A programmable apparatus which executes any of the above mentioned computer program products or computer implemented methods may include one or more processors, microprocessors, microcontrollers, embedded microcontrollers, programmable digital signal processors, programmable devices, programmable gate arrays, programmable array logic, memory devices, application specific integrated circuits, or the like. Each may be suitably employed or configured to process computer program instructions, execute computer logic, store computer data, and so on.

It will be understood that a computer may include a computer program product from a computer-readable storage medium and that this medium may be internal or external, removable and replaceable, or fixed. In addition, a computer may include a Basic Input/Output System (BIOS), firmware, an operating system, a database, or the like that may include, interface with, or support the software and hardware described herein.

Embodiments of the present invention are not limited to applications involving conventional computer programs or programmable apparatus that run them. It is contemplated, for example, that embodiments of the presently claimed invention could include an optical computer, quantum computer, analog computer, or the like. A computer program may be loaded onto a computer to produce a particular machine that may perform any and all of the depicted functions. This particular machine provides a means for carrying out any and all of the depicted functions.

Any combination of one or more computer readable media may be utilized. The computer readable medium may be a non-transitory computer readable medium for storage. A computer readable storage medium may be electronic, magnetic, optical, electromagnetic, infrared, semiconductor, or any suitable combination of the foregoing. Further computer readable storage medium examples may include an electrical connection having one or more wires, a portable computer diskette, a hard disk, a random access memory (RAM), a read-only memory (ROM), an erasable programmable read-only memory (EPROM), Flash, MRAM, FeRAM, phase change memory, an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

It will be appreciated that computer program instructions may include computer executable code. A variety of languages for expressing computer program instructions may include without limitation C, C++, Java, JavaScript™, ActionScript™, assembly language, Lisp, Perl, Tcl, Python, Ruby, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed more or less simultaneously to enhance utilization of the processor and to facilitate substantially simultaneous functions. By way of implementation, any and all methods, program codes, program instructions, and the like described herein may be implemented in one or more thread. Each thread may spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described. Further, the method steps shown are intended to include any suitable method of causing one or more parties or entities to perform the steps. The parties performing a step, or portion of a step, need not be located within a particular geographic location or country boundary. For instance, if an entity located within the United States causes a method step, or portion thereof, to be performed outside of the United States then the method is considered to be performed in the United States by virtue of the entity causing the step to be performed.

While the invention has been disclosed in connection with preferred embodiments shown and described in detail, various modifications and improvements thereon will become apparent to those skilled in the art. Accordingly, the spirit and scope of the present invention is not to be limited by the foregoing examples, but is to be understood in the broadest sense allowable by law.

What is claimed is:

1. A computer implemented method for affect based recommendations comprising:
   playing a first media presentation to an individual;
   capturing mental state data, wherein the mental state data includes facial data, for the individual, while the first media presentation is played;
   inferring mental states, using one or more processors, based on the mental state data which was collected and analysis of the facial data for at least brow furrows;
   correlating the mental state data which was captured for the individual to mental state data collected from other people who experienced the first media presentation wherein the correlating is based on identifying and using maximally dissimilar responses during part of the correlating;
   ranking the first media presentation relative to another media presentation based on the mental state data which was captured, wherein the ranking is for the individual based on the mental state data captured from the individual; and
   recommending a second media presentation to the individual based on the mental state data for the individual which was captured wherein the recommending the second media presentation to the individual is further based on the correlating between the individual and the other people.

2. The method of claim 1 further comprising analyzing the mental state data to produce mental state information.

3. The method according to claim 1 wherein the first media presentation includes one of a group consisting of a movie, a television show, a web series, a webisode, a video, a video clip, an electronic game, an e-book, and an e-magazine.

4. The method according to claim 1 wherein the second media presentation includes one of a group consisting of a movie, a television show, a web series, a webisode, a video, a video clip, an electronic game, an e-book, and an e-magazine.

5. The method according to claim 1 wherein the first media presentation is played on a web-enabled interface.

6. The method according to claim 1 wherein the first media presentation includes one of a YouTube™, a Vimeo™ video, and a Netflix™ video.

7. The method according to claim 1 wherein the second media presentation includes one of a YouTube™, a Vimeo™ video, and a Netflix™ video.

8. The method of claim 1 wherein the ranking is based on anticipated preferences for the individual.

9. The method according to claim 1 wherein the mental state data is captured from multiple people and further comprising aggregating the mental state data from the multiple people.

10. The method of claim 9 further comprising ranking the first media presentation relative to another media presentation based on the mental state data which was aggregated from the multiple people.

11. The method of claim 9 wherein the analysis is performed on an analysis server.

12. The method of claim 11 wherein the analysis server provides aggregated mental state information for the multiple people.

13. The method of claim 9 wherein the aggregating recognizes trends for the individual and determines correlation vectors for the individual and the multiple people.

14. The method of claim 13 wherein correlation is determined using a weighted distance evaluation between two vectors of the correlation vectors.

15. The method of claim 14 wherein the recommending is based on one of the two vectors being a sufficiently small distance from another of the two vectors.

16. The method of claim 14 wherein the correlation is further based on a weighted Euclidean or Mahalanobis distance.

17. The method of claim 1 wherein the mental state data further includes physiological data or actigraphy data.

18. The method of claim 17 wherein the physiological data includes one or more of electrodermal activity, heart rate, heart rate variability, skin temperature, and respiration.

19. The method of claim 1 wherein the facial data includes information on one or more of a group consisting of facial expressions, action units, head gestures, smiles, squints, lowered eyebrows, raised eyebrows, smirks, and attention.

20. The method according to claim 1 wherein the mental states include one of a group consisting of sadness, happiness, frustration, confusion, disappointment, hesitation, cognitive overload, focusing, being engaged, attending, boredom, exploration, confidence, trust, delight, valence, skepticism, and satisfaction.

21. The method according to claim 1 wherein the playing of the first media presentation is done on a mobile device and further comprising recording of facial images with the mobile device as part of the capturing of the mental state data.

22. The method of claim 1 wherein the correlating is based on identifying similar likes.

23. A computer program product embodied in a non-transitory computer readable medium comprising:
   code for playing a first media presentation to an individual;
   code for capturing mental state data, wherein the mental state data includes facial data, for the individual while the first media presentation is played;
   code for inferring mental states, executed on one or more processors, based on the mental state data which was collected and analysis of the facial data for at least brow furrows;

code for correlating the mental state data which was captured for the individual to mental state data collected from other people who experienced the first media presentation wherein the correlating is based on identifying and using maximally dissimilar responses during part of the correlating;

code for ranking the first media presentation relative to another media presentation based on the mental state data which was captured; and code for recommending a second media presentation to the individual based on the mental state data for the individual which was captured wherein the recommending the second media presentation to the individual is further based on the correlating between the individual and the other people.

24. A computer system for affect based recommendations comprising:

a memory for storing instructions;

one or more processors attached to the memory wherein the one or more processors are configured to:

play a first media presentation to an individual;

capture mental state data, wherein the mental state data includes facial data, for the individual while the first media presentation is played;

infer mental states, using the one or more processors, based on the mental state data which was collected and analysis of the facial data for at least brow furrows;

correlate the mental state data which was captured for the individual to mental state data collected from other people who experienced the first media presentation wherein correlation is based on identifying and using maximally dissimilar responses during part of the correlation;

rank the first media presentation relative to another media presentation based on the mental state data which was captured; and recommend a second media presentation to the individual based on the mental state data for the individual which was captured wherein recommendation of the second media presentation to the individual is further based on correlation between the individual and the other people.

25. A computer implemented method for affect based ranking comprising:

displaying a plurality of media presentations to a group of people;

capturing mental state data, wherein the mental state data includes facial data, from the group of people while the plurality of media presentations is displayed;

inferring mental states, using one or more processors, based on the mental state data which was collected and analysis of the facial data for at least brow furrows;

correlating the mental state data captured from the group of people who viewed the plurality of media presentations wherein the correlating is based on identifying and using maximally dissimilar responses during part of the correlating;

ranking the first media presentation relative to another media presentation based on the mental state data which was captured; and ranking the media presentations relative to one another based on the mental state data.

26. The method according to claim 25 further comprising tagging the plurality of media presentations with mental state information based on the mental state data which was captured.

* * * * *